US008696359B2

(12) United States Patent
Clark et al.

(10) Patent No.: US 8,696,359 B2
(45) Date of Patent: Apr. 15, 2014

(54) METHODS OF ASSESSING COGNITIVE DYSFUNCTION

(75) Inventors: Luke Clark, Cambridge (GB); Trevor W. Robbins, Cambridge (GB)

(73) Assignee: Cambridge University Technical Services Limited, Cambridge, Cambridgeshire (GB)

( * ) Notice: Subject to any disclaimer, the term of this patent is extended or adjusted under 35 U.S.C. 154(b) by 1689 days.

(21) Appl. No.: 11/632,835

(22) PCT Filed: Jul. 19, 2004

(86) PCT No.: PCT/GB2004/003136
§ 371 (c)(1),
(2), (4) Date: Apr. 17, 2008

(87) PCT Pub. No.: WO2006/008428
PCT Pub. Date: Jan. 26, 2006

(65) Prior Publication Data
US 2009/0012713 A1     Jan. 8, 2009

(51) Int. Cl.
*G09B 19/00* (2006.01)
(52) U.S. Cl.
USPC .......................................... 434/236
(58) Field of Classification Search
USPC ..................... 434/236, 238; 702/19
See application file for complete search history.

(56) References Cited

U.S. PATENT DOCUMENTS

| | | | | |
|---|---|---|---|---|
| 6,044,292 | A * | 3/2000 | Heyrend et al. | 600/544 |
| 6,534,063 | B1 * | 3/2003 | Fallon | 424/198.1 |
| 6,884,078 | B2 * | 4/2005 | Wiig et al. | 434/236 |
| 2002/0192624 | A1 * | 12/2002 | Darby et al. | 434/236 |

FOREIGN PATENT DOCUMENTS

| | | |
|---|---|---|
| JP | 2004-135824 | 5/2004 |
| JP | 2005-13713 | 1/2005 |
| JP | 2005-508211 | 3/2005 |
| JP | 2005-515804 | 6/2005 |
| WO | WO-03/015059 | 2/2003 |
| WO | WO-03/034919 | 5/2003 |

OTHER PUBLICATIONS

Canadian Office Action issued Sep. 19, 2011, directed to Canadian Application No. 2,575,247; 4 pages.
International Preliminary Report on Patentability mailed on Feb. 1, 2007 for International Patent Application No. PCT/GB2004/003136. 5 pages.
Allen, T. J. et al., (1998). "Impulsivity and History of Drug Dependence," *Drug and Alcohol Dependence* 50: 137-145.

(Continued)

*Primary Examiner* — Kesha Frisby
(74) *Attorney, Agent, or Firm* — Morrison & Foerster LLP

(57) ABSTRACT

This invention relates to methods and means for assessing cognitive dysfunction, in particular impulsivity associated cognitive dysfunction, which may for example include Attention Deficit Hyperactivity Disorder (ADHD), substance abuse, and non-toxic addictive/compulsive behavior. A method may comprise displaying a population of elements to the individual and allowing the sequential selection of elements within the population by the individual. The selection of an element reveals to the individual a characteristic of the selected element which is one of a number of possible characteristics of elements in said population. The sequential selection ends when the individual chooses which of the possible characteristics is possessed by the most elements in the population. The number of elements selected by the individual in making this choice is then correlated to the likelihood that the individual has impulsivity associated cognitive dysfunction.

34 Claims, 3 Drawing Sheets

(56) References Cited

OTHER PUBLICATIONS

Aron, A. R. et al. (Apr. 2004). "Inhibition and the Right Inferior Frontal Cortex," *TRENDS in Cognitive Sciences* 8(4): 170-177.
Ault, R. L. et al. (Mar. 1976). "Some Methodological Problems in Reflection-Impulsivity Research," *Child Development* 47(1): 227-231.
Barratt, E. S. (1965). "Factor Analysis of Some Psychometric Measures of Impulsiveness and Anxiety," *Psychological Reports* 16: 547-554.
Bentler, P. M. et al. (Mar. 1976). "A Multitrait-Multimethod Analysis of Reflection-Impulsivity," *Child Development* 47(1): 218-226.
Bickel, W. K. et al. (2001). "Toward a Behavioral Economic Understanding of Drug Dependence: Delay Discounting Process," *Addiction* 96: 73-86.
Block, J. et al. (1974). "Some Misgivings About the Matching Familiar Figures Test as a Measure of Reflection-Impulsivity," *Developmental Psychology* 10(5): 611-632.
Cowan, R. L. et al. (2003). "Reduced Cortical Gray Matter Density in Human MDMA (Ecstasy) Users: A Voxel-based Morphometry Study," *Drug and Alcohol Dependence* 72: 225-235.
Dawes, M. A. et al. (1997). "Behavioral Self-Regulation: Correlates and 2 Year Follow-ups for Boys at Risk for Substance Abuse," *Drug and Alcohol Dependence* 45: 165-176.
Di Chiara, G. et al. (Jul. 1988). "Drugs Abused by Humans Preferentially Increase Synaptic Dopamine Concentrations in the Mesolimbic System of Freely Moving Rats," *Proceedings of the National Academy of Sciences* 85: 5274-5278.
Dickman, S. J. (1990). "Functional and Dysfunctional Impulsivity: Personality and Cognitive Correlates," *Journal of Personality and Social Psychology* 58(1): 95-102.
Evenden, J. L. (1999). "Varieties of Impulsivity," *Psychopharmacology* 146: 348-361.
Fillmore, M. T. et al. (2002). "Impaired Inhibitory Control of Behavior in Chronic Cocaine Users," *Drug and Alcohol Dependence* 66: 265-273.
Fox, H. C. et al. (May 2002). "Neuropsychological Evidence of a Relatively Selective Profile of Temporal Dysfunction in Drug-Free MDMA ('Ecstasy') Polydrug Users," *Psychopharmacology* 162: 203-214.
Kagan, J. (1966). "Reflection-Impulsivity: The Generality and Dynamics of Conceptual Tempo," *Journal of Abnormal Psychology* 71(1): 17-24.
Koob, G. F. et al. (Nov. 1988). "Cellular and Molecular Mechanisms of Drug Dependence," *Science* 242(4879): 715-723.
Matochik, J. A. et al. (2003). "Frontal Cortical Tissue Composition in Abstinent Cocaine Abusers: A Magnetic Resonance Imaging Study," *NeuroImage* 19: 1095-1102.
Messer, S. B. (1976). "Reflection-Impulsivity: A Review," *Psychological Bulletin* 83(6): 1026-1052.
Moeller, F. G. et al. (Nov. 2001). "Psychiatric Aspects of Impulsivity," *American Journal of Psychiatry* 158(11): 1783-1793.
Moeller, F. G. et al. (2002). "Increased Impulsivity in Cocaine Dependent Subjects Independent of Antisocial Personality Disorder and Aggression," *Drug and Alcohol Dependence* 68: 105-111.
Morgan, M. J. et al. (Oct. 2001). "Ecstasy (MDMA): Are the Psychological Problems Associated With Its Use Reversed by Prolonged Abstinence?" *Psychopharmacology* 159: 294-303.
Paulus, M. P. et al. (2003). "Decision Making by Methamphetamine-Dependent Subjects is Associated with Error-Rate-Independent Decrease in Prefrontal and Parietal Activation," *Society of Biological Psychiatry* 53: 65-74.
Roberts, A. C. et al. (Mar. 2000). "Inhibitory Control and Affective Processing in the Prefrontal Cortex: Neuropsychological Studies in the Common Marmoset," *Cerebral Cortex* 10(3): 252-262.
Salo, R. et al. (2002). "Preliminary Evidence of Reduced Cognitive Inhibition in Methamphetamine-Dependent Individuals," *Psychiatry Research* 111: 65-74.
Sekine, Y. et al. (Sep. 2003). "Association of Dopamine Transporter Loss in the Orbitofrontal and Dorsolateral Prefrontal Cortices with Methamphetamine-Related Psychiatric Symptoms," *American Journal of Psychiatry* 160(9): 1699-1701.
Swann, A. C. et al. (2002). "Two Models of Impulsivity: Relationship to Personality Traits and Psychopathology," *Society of Biological Psychiatry* 51: 988-994.
Tarter, R. E. et al. (Feb. 2004). "Neurobehavior Disinhibition in Childhood Predisposes Boys to Substance Use Disorder by Young Adulthood: Direct and Mediated Etiologic Pathways," *Drug and Alcohol Dependence* 73: 121-132.
Volkow, N. D. (Dec. 2001). "Low Level of Brain Dopamine $D_2$ Receptors in Methamphetamine Abusers: Association with Metabolism in the Orbitofrontal Cortex," *American Journal of Psychiatry* 158(12): 2015-2021.
Wang, G. J. et al. (Feb. 2001). "Brain Dopamine and Obesity," *The Lancet* 357: 354-357.
Whiteside, S. P. et al. (2001). "The Five Factor Model and Impulsivity: Using a Structural Model of Personality to Understand Impulsivity," *Personality and Individual Differences* 30: 669-689.
Japanese Notice of Reasons for Rejection mailed May 12, 2010, directed to Japanese Application No. 2007-522000; 4 pages.

\* cited by examiner

METHODS OF ASSESSING COGNITIVE DYSFUNCTION

This invention relates to methods and means for the assessment of cognitive dysfunction, in particular impulsivity associated cognitive dysfunction.

Laboratory tasks which directly evoke brain mechanisms of impulsivity have been developed using cognitive and behavioural models of impulsivity. A number of cognitive and behavioural models exist and the degree to which these 'varieties' of impulsivity are dissociable, or tap the same common construct, remains unclear (Evenden, 1999; Moeller et al., 2001; Aron et al., 2004).

Tasks of motor inhibition, including the Go-No Go task and Stop Signal task, establish an automatic behaviour (usually a button press) that must be inhibited on occasional trials. Impaired motor inhibition is a cardinal symptom of Attention Deficit Hyperactivity Disorder (ADHD; Logan et al 2000), and has been demonstrated more recently in cocaine addicts (Fillmore and Rush, 2002) and methamphetamine-dependent individuals (Salo et al., 2002).

The delayed reward paradigm assesses choice preferences for a small reward available after a short delay versus larger rewards available further in the future (Mazur, 1987). Impulsivity is defined by preference for the short delay rewards, relating to impaired delay of gratification. Delayed reward preferences can be assessed with questionnaires using hypothetical scenarios (e.g. "Would you prefer $10 now or $100 in one week?") or directly using laboratory tests. Both methods have, for example, demonstrated sensitivity to substance dependence to a range of drugs (Bickel and Marsch, 2001; Moeller et al., 2002).

A third variety of impulsivity has been called 'reflection impulsivity'. Reflection occurs during many cognitive operations involving decision-making or problem-solving, at a stage prior to response, when task-relevant information must be evaluated and the adequacy of a solution must be considered (Kagan, 1966). Insufficient reflection will inevitably reduce the quality of the eventual decision. Reduced reflection may, for example, characterised certain forms of cognitive dysfunction and may also contribute to recreational drug use and substance dependence.

The standard test of reflection impulsivity is the Matching Familiar Figures Test (MFFT; Kagan, 1966). In this test, the subject is presented with a template picture (e.g. a bicycle) and six similar variants. One variant is identical to the template, and must be identified on each trial. Children with hyperactivity disorders (including ADHD) perform more impulsively than control children on the MFFT, with shorter response latencies and more incorrect responses (Messer 1976; Sandoval 1977), with improvement in performance following treatment with methylphenidate (Brown & Sleator, 1979), the benchmark pharmacological treatment for ADHD. Successful MFFT performance requires substantial visual search to identify the dimensions on which the variants differ from the template. Visual working memory, iconic memory, and a degree of strategy use must then be employed to compare the variants against the template. Impairments in these domains increase errors on the MFFT irrespective of impulsivity (Block et al., 1974). Neuropsychological tests more suitable for assessing impulsivity associated dysfunction in adult clinical populations are required The present inventors have produced a reflection-impulsivity test that allows the assessment of impulsivity associated cognitive dysfunction in adult populations, including for example, conditions such as attention deficit hyperactivity disorder and substance abuse.

One aspect of the invention provides a method of assessing an individual for impulsivity associated cognitive dysfunction may comprise;
i. displaying a population of elements to the individual,
ii. allowing the individual to select an element from the population,
iii. revealing to the individual a characteristic of the selected element, the characteristic being a member of a set of possible characteristics of elements in said population,
iv. repeating steps ii and iii until the individual decides which of the characteristics from the set is possessed by the most elements in the population,
v. correlating the number of elements selected by the individual with the probability that the individual has impulsivity associated cognitive dysfunction.

In some embodiments, a characteristic from the set of characteristics may be assigned to an element selected by the individual. The assigned characteristic is then revealed to the individual.

For example, a method of assessing an individual for impulsivity associated cognitive dysfunction may comprise;
i. displaying a population of elements to the individual,
ii. allowing the individual to select an element from the population,
iii. assigning a characteristic to the selected element, wherein the characteristic is one of a set of possible characteristics of elements in said population,
iv. revealing to the individual the characteristic assigned to the selected element,
v. repeating steps ii, iii and iv until the individual decides which of the characteristics from the set is possessed by the most elements in the population, and
vi. correlating the number of elements selected by the individual with the probability that the individual has impulsivity associated cognitive dysfunction.

In other embodiments, the elements in the population may each be assigned a characteristic from the set of characteristics prior to the selection of elements by the individual. The characteristic assigned to an element is concealed until the individual selects that element.

For example, a method of assessing an individual for impulsivity associated cognitive dysfunction comprising;
i. displaying a population of elements to the individual, wherein each element is assigned one of a set of characteristics, the characteristics assigned to the elements being concealed from the individual,
ii. allowing the individual to select an element from the population,
iii. revealing to the individual the characteristic possessed by the element selected,
iv. repeating steps ii and iii until the individual decides which of the characteristics from the set is possessed by the most elements in the population,
v. correlating the number of elements selected by the individual possessing each characteristic with the probability that the individual has impulsivity associated cognitive dysfunction.

In some embodiments, a method of assessing an individual for impulsivity associated cognitive dysfunction, such as attention deficit hyperactivity disorder, may comprise;
displaying a population of elements to the individual,
allowing the sequential selection of elements within the population by the individual, wherein the selection of an element reveals to the individual a characteristic of the selected element,
the revealed characteristic being a member of a set of possible characteristics of elements in said population, said sequential selection ending when the individual chooses which of the set of characteristics is possessed by the most elements in the population and;

correlating the number of elements selected by the individual to the probability that said individual has impulsivity associated cognitive dysfunction, for example attention deficit hyperactivity disorder.

Although they may differ in the assigned characteristic, the elements in the population are preferably otherwise identical and may be of any shape or form. In some preferred embodiments, the elements may be in a form that is suitable for tessellating a plane or surface, such as a square, rectangle or hexagon. This allows the population to be displayed as a solid shape or form, without gaps. Preferably, the elements of the population are squares or boxes.

The population may consist of 5 to 100 elements, preferably 9 to 64 elements, for example 9, 16, 25, or 36 elements. In preferred embodiments, the population consists of 25 elements.

The population may be arranged in any configuration or arrangement. In preferred embodiments, in particular when the elements are squares or boxes, the population may be arranged in a square matrix, for example a 5×5 matrix with 25 constituent elements.

The set of characteristics possessed by elements in the population may consist of two, three, four or more distinct characteristics. In preferred embodiments, the set of characteristics consists of two characteristics.

Suitable characteristics include numbers, letters, colours, shapes, icons or pictures.

In some embodiments, each element possesses a colour, for example either yellow or blue, which is initially concealed from the individual and which is revealed to the individual by selecting that element. Thus, prior to selection, the elements may all be the same colour, preferably a colour which is not one of the concealed colours, for example grey.

The elements may be displayed by any convenient means. In preferred embodiments, the population of elements is provided by a data processing means and displayed on a monitor or other image display.

Elements within the population are selected one by one by the individual. The characteristic of the selected element is revealed to the individual before the next element is selected. For example, upon selection by the individual, the selected element may assume its characteristic colour.

The selection of an element by the individual may be registered by any convenient means. For example, when the population of elements is displayed on a monitor or other image display, the individual may select an element from the displayed population by means of a graphic interface. The element may be selected from the population displayed on the monitor using a touch sensitive monitor, a keypad, touchpad, mouse, trackball, pressure-sensitive stylus, or other interface device. Suitable graphic interfaces and interface devices are well known in the art.

In some embodiments, the characteristic which is revealed when the individual selects an element may be part of a sequence of characteristics which are progressively revealed as the elements from population are selected, irrespective of which element within the population is selected. The sequence may be preordained or fixed and may be a random or non-random sequence.

For example, the same random sequence may be used to assess different individuals or the same individual at different times to allow comparison of the results.

A non-random sequence of characteristics may be biased towards a particular characteristic i.e. all or part of the sequence may contain an increased proportion of one member of the set of characteristics, relative to other members of the set. For example, the early parts of the sequence of characteristics may contain an increased proportion of one characteristic (for example two or more consecutive elements having that characteristic) in order to favour the choice of that characteristic.

In other embodiments, a characteristic may be assigned to each element in the population prior to the selection of elements by the individual. Characteristics may be assigned randomly or in accordance with a fixed ratio of each characteristic from the set of characteristics.

The individual may be instructed on the actions required of him or her. For example, a method may include instructing the individual to sequentially select elements from the population and then to decide or choose which one of the set of characteristics is possessed by the most elements in the population. In preferred embodiments, for example when the set consists of two characteristics, the individual may be instructed to decide which characteristic is possessed by the majority of elements in the population.

Instructions to the individual may be audible, for example by a recording or other means, or in written or graphic form, for example, instructions displayed on a monitor or other image display.

A method may further comprise registering the characteristic which the individual decides is possessed by the majority of the elements in the population.

The characteristic may be stored and/or recorded for further analysis. For example, the characteristic which the individual decides is possessed by the most elements in the population may be compared to the actual characteristic possessed by the most elements in the population, and the accuracy of the decision determined.

The choice of characteristic may be registered by any convenient means. For example, all the members of the set of characteristics may be displayed, for example on a monitor, and the characteristic which the individual deems to be possessed by the most elements in the population may be chosen from the displayed set of characteristics. When the set is displayed on a monitor, the characteristic may be chosen through an graphic interface such as a touch sensitive screen. The choice may then be recorded and/or stored.

The number of elements from the population which were selected by the individual before choosing a characteristic may be determined and/or recorded.

The number of selected elements possessing each characteristic from the set of characteristics may also be determined and/or recorded.

The probability coefficient for a correct response from the number of elements selected by the individual may be calculated and/or determined.

The probability co-efficient is related to the number of elements selected and provides an accurate measure of the level of certainty that is tolerated by the individual in making a decision. The skilled person may calculate the probability co-efficient for any assessment method described herein using standard statistical techniques. For example, for an assessment method in which an element may possess one of two possible characteristics, the probability co-efficient may be determined from the formula:

$$P(\text{correct}) = \sum_{A}^{z} Z choose A / 2^z$$

where z=(total number of elements)−(number of elements selected), and
A=(minimum number of elements required for a majority in the population)−(the number of elements visible with the chosen characteristic).
Thus, for a population of 25 elements;
z=25−(number of elements selected), and;
A=13−(the number of elements visible with the chosen characteristic).
For example, if the individual decides, after selecting 10 elements (8 red, 2 blue), that the red elements are in the majority, then z=25−10=15, a=13−8=5, and; P(corr)= [15!/(10!*5!)+15!/(9!*6!)+ . . . +15!/(0!*15!)]/$2^{15}$=0.94

Preferably, the methods described herein (e.g. steps i to v above) are performed more than once, for example 5 to 100 times, more preferably 10, 15 or 20 times. The sequence or distribution of the characteristics in the population will be different each time the method is performed.

The interval between repeats of the assessment tests may be varied in accordance with the time taken to perform each repetition in order to provide a minimum delay between tests. A suitable minimum delay may be 30 s.

The methods described herein may comprise a scoring system. The individual may, for example, be instructed to score or accrue the maximum number of points over one or more repetitions of the assessment test.

The individual may be awarded points for deciding correctly that a characteristic is possessed by the majority of the elements in the population and/or may lose points for deciding incorrectly that a characteristic is possessed by the majority of the elements in the population (i.e. choosing a characteristic that is not possessed by the majority of the elements in the population).

In some embodiments, the individual may lose points for each element selected by the individual before deciding on or registering a characteristic.

The total number of points accrued by the individual and/or the number of points lost or gained at any stage may be displayed.

The average number of elements selected by the individual over all the performances of the assessment test may also be determined.

The number of elements selected from the population possessing each characteristic may also be determined for each performance of the assessment test.

The number of incorrect decisions made by the individual over all the performances of the assessment test may be determined and the error rate calculated. The correlation of the number of elements selected with the number of errors made in choosing a characteristic may be determined. Reduced selection of elements will generally be associated with more errors The average probability coefficient at which the individual chooses a characteristic may be determined from the average number of elements selected by the individual over the repetitions and/or the probability coefficients for each individual performance of the test.

From the parameters determined, the individual may be assessed for impulsivity associated cognitive dysfunction.

For example, a low average probability of a correct response when deciding a characteristic, relative to a healthy control, for example an average probability coefficient of less than 0.77, may be indication of impulsivity associated cognitive dysfunction.

In some embodiments, a low average number of elements selected before deciding a characteristic, relative to a healthy control, for example less than 11 elements from a 25 element population, may be indicative of impulsivity associated cognitive dysfunction.

An impulsivity associated cognitive dysfunction, in particular a reflection-impulsivity associated cognitive dysfunction may include Attention Deficit Hyperactivity Disorder (ADHD: also known as Attention Deficient Disorder (ADD)), substance abuse, non-toxic addictive/compulsive behaviours such as pathological gambling and over-eating, the manic phase of bipolar disorder, personality disorders including psychopathy, and neurological problems including frontal dementias and behavioural syndromes arising from frontal injury e.g. by brain tumour or closed head injury.

Substance abuse may include current substance abuse, previous substance abuse or susceptibility to substance abuse. Substance of abuse may include cocaine, amphetamine, benzodiazepine, MDMA, alcohol and/or opiates.

An individual suitable for assessment with a method described herein may have been identified by other means as a candidate for impulsivity associated cognitive dysfunction by other means. For example, an individual may be known or suspected of suffering from impulsivity associated cognitive dysfunction as described above by a medical practitioner. For example, the individual may display other symptoms or behaviours characteristic of dysfunction. The individual may display one or more symptoms which allow a diagnosis of impulsivity associated neuropsychiatric condition. Neuropsychiatric diagnostic criteria are set out, for example in the Diagnostic and Statistical Manual of Mental Disorders (text revision), American Psychiatric Association (2000) American Psychiatric Publishing Inc (DSM-IV-TR).

In other embodiments, an individual suitable for assessment may have no previous association with impulsivity associated cognitive dysfunction. For example the individual may show no symptoms or behaviours characteristic of impulsivity dysfunction. Individuals identified by the present methods as having a high probability of impulsivity associated cognitive dysfunction may be assessed further using other neuropsychological and diagnostic criteria.

Further aspects of the invention provide methods and means of screening for compounds useful in the treatment of impulsivity associated cognitive dysfunction.

A method of identifying and/or obtaining a compound useful in the treatment of impulsivity associated cognitive dysfunction may comprise;
    administering a test compound to an individual, and;
    determining the impulsivity of the individual using a method described herein.

A reduction in impulsivity may be indicative that the compound is a candidate compound for use in the treatment of impulsivity associated cognitive dysfunction.

Impulsivity associated cognitive dysfunction is described in more detail above.

Impulsivity maybe determined relative to a control, for example an individual who has received a placebo.

Preferably, the individual is a member of a population. A method may thus comprise;
    administering a test compound to a population of individuals, and;

determining the impulsivity of said population using a method described herein.

An improvement in performance i.e. a reduction in impulsivity, for example relative to a control population, may be indicative that the compound is a candidate compound for use in the treatment of impulsivity associated cognitive dysfunction.

An individual or population suitable for use in such methods may be normal and non-clinical or may be suffering from or susceptible to impulsivity associated cognitive dysfunction as described above.

Any pharmaceutical agent with a suitable safety profile for administration to a human may be employed as a test compound. A compound may be a known compound for use in treating impulsivity associated cognitive dysfunction, such as methylphenidate, ritalin or atomoxetine, or other compounds, such as amphetamines.

Protocols and approaches for performing such methods, including the provision of suitable controls, are well known to the skilled person.

Further aspects of the invention provide methods and means for assessing treatments for impulsivity associated cognitive dysfunction.

A method of assessing a treatment for impulsivity associated cognitive dysfunction may comprise;
    determining the impulsivity of an individual being treated for impulsivity associated cognitive dysfunction using a method as described herein at a first and a second time point,
    determining changes in impulsivity at the first and second time points.

An individual may, for example be undergoing treatment with a pharmaceutical agent such as methylphenidate or ritalin, which are known for use in the treatment of ADHD.

The treatment may be monitored periodically, for example weekly or monthly to assess its effect. Impulsivity may thus be assessed at a number of time points during the treatment. Impulsivity may also be determined before and after the treatment.

Further aspects of the invention provide: (i) computer-readable code for performing a method described herein, (ii) a computer program product carrying such computer-readable code, and (iii) a computer system configured to perform a method described herein.

The term "computer program product" includes any computer readable medium or media which can be read and accessed directly by a computer. Typical media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

A typical computer system of the present invention comprises a central processing unit (CPU), input means, output means and data storage means (such as RAM). A monitor or other image display is preferably provided.

The input means may comprise a touch sensitive monitor or other graphic interface device which allows the selection of elements and choice of the characteristic which the individual decides is possessed by the most elements in the population.

For example, a computer system may comprise a processor adapted to perform a method of the invention. For example the processor may be adapted to:
i. display a population of elements to the individual,
ii. allow the individual to select an element from the population,
iii. reveal to the individual a characteristic of the selected element, the characteristic being a member of a set of possible characteristics of elements in said population,
iv. repeat steps ii and iii until the individual decides which of the characteristics from the set is possessed by the most elements in the population,
v. correlate the number of elements selected by the individual with the impulsivity of said individual and/or the probability that said individual has an impulsivity associated cognitive dysfunction as described herein.

In particular, a computer system according to the invention may comprise a processor adapted to;
1. display a matrix of boxes to an individual,
2. allow the individual to select a box from the population,
3. reveal to the individual the colour of the selected box, each box in the matrix having one of two possible colours
4. repeat steps 2 and 3 until the individual chooses which of the two colours is possessed by the majority of boxes in the matrix; and,
5. correlate the number of elements selected by the individual with the impulsivity of said individual and/or the probability that said individual has an impulsivity associated cognitive dysfunction as described herein.

In some embodiments, the processor may further be adapted to assign a characteristic from the set of characteristics to an element. For example, the processor may be adapted to assign a characteristic from the set of characteristics to a selected element and then to reveal the assigned characteristic to the individual. The processor may be adapted to store a fixed sequence of characteristics which are progressively assigned to elements as they are selected. The sequence may be inputted into the processor prior to operation or may be generated automatically by the processor.

The processor may be adapted to calculate the average probability coefficient for an individual as described herein.

The computer system may further comprise a memory device for storing the number of selections and the characteristic chosen in each repetition of the test. The memory device may be adapted for storing assessment test results from a number of different individuals. Statistics and data derived from these test results, for example an probability coefficient or impulsivity score for an individual or a probability that an individual has a cognitive dysfunction, may be stored on another or the same memory device, and/or may be sent to an output device or displayed on a monitor.

Another aspect of the invention provides an test device for assessing an individual for an impulsivity associated cognitive dysfunction comprising a display, a graphic interface and a processor adapted for use in a method described herein.

Various further aspects and embodiments of the present invention will be apparent to those skilled in the art in view of the present disclosure. All documents mentioned in this specification are incorporated herein by reference in their entirety.

Certain aspects and embodiments of the invention will now be illustrated by way of example and with reference to the figures and tables described below.

FIG. 1 shows the mean performance on the novel reflection-impulsivity task in three groups of subjects categorised into three groups on the matching familiar figures test. Defined from median splits on accuracy and (correct response) latency, high impulsives show fast, inaccurate responding; low impulsives show slow, accurate responding; intermediates fall into the other two quadrants (slow, inaccurate/fast, accurate). Errors bar represent SEM.

Table 1 shows the performance on the RIT, MFFT and BIS-11 in healthy undergraduates separated using median splits on MFFT performance.

Table 2 shows the group characteristics of amphetamine, opiate, ex-users and non-drug using controls in experiment 2.

Table 3 shows the percentage of subjects with current or past abuse of other substances in the amphetamine, opiate, ex-users and non-drug using controls in experiment 2.

Table 4 shows RIT performance and BIS ratings in the amphetamine, opiate, ex-users and non-drug using controls in experiment 2.

Experiment 1

Methods 40 healthy undergraduate students at the University of Cambridge (19 male, 21 female) aged 18-23 were recruited by word of mouth. Subjects were administered the novel Reflection-Impulsivity Task (RIT) and the MFFT in fixed order. These measures were administered on a Datalux PC with 10.5 inch touchscreen monitor. Subjects completed the Barratt Impulsivity Scale version 11 (BIS; Patton et al. 1995) and a drug and alcohol-screening questionnaire prior to testing. Subjects completed written informed consent prior to testing, which was approved by the Local Research Ethics Committee.

Reflection Impulsivity Task (RIT).

Figure 1:
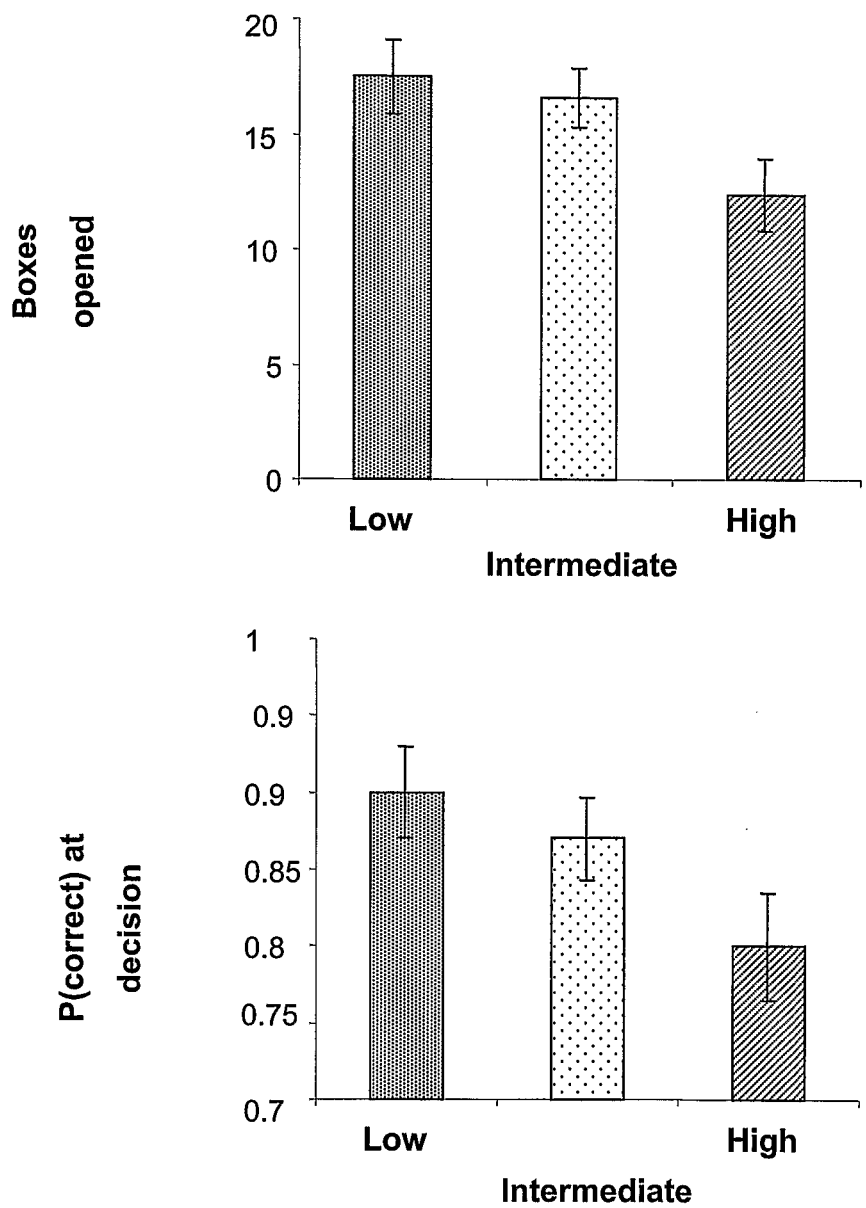

The task was programmed in Microsoft Visual Basic 6.0 and administered on a touch-sensitive monitor. Subjects completed 10 trials in each of 2 conditions: the Fixed Reward condition and the Reward Conflict condition, which were counter-balanced for order across subjects. A screen display is presented in FIG. 1. On each trial, subjects were presented with a 5×5 matrix of grey boxes (each 23 mm×23 mm), with two larger coloured panels at the foot of the screen. Touching a grey box caused the box to open (immediately) to reveal one of the two colours at the foot of the screen. The subject was instructed: "You are about to play a game for points. The game will take 10 minutes to complete. It consists of two parts and on each part there will be 10 gos. On every go, you will be able to see 25 boxes on the screen. Initially, the boxes will all be greyed out, but when you pick a box, it will reveal itself to be one of two colours. Your task is to decide which colour you think is in the majority. It is entirely up to you how many boxes you open before making your decision. When you have made your decision, you should touch that colour panel at the bottom of the screen." These instructions were read to the subject during a practice trial where 100 points were available to win or lose for a correct or wrong response. This practice trial was identical to the Fixed Reward condition, where it was further reiterated: "You will win 100 points if you pick the correct colour, regardless of how many boxes you open, and you can open as many boxes as you wish. You will lose 100 points if you get it wrong. Try to win as many points as you can." In the Reward Conflict condition, 250 points were available to win at the start of the trial, which decreased by 10 points with each box opened, thereby creating a conflict between the level of certainty and the reward available. Prior to commencing the reward conflict condition, subjects were instructed: "On these gos, the amount you can win will drop by 10 points with every box you uncover, therefore the earlier you make your decision the more points you will win if you are right. If you are wrong, you will lose 100 points regardless of when you make your decision. Try to win as many points as you can."

Subjects were able to open the boxes at their own rate. On touching one the coloured panels, the remaining boxes were uncovered and a feedback message "Correct! You have won [x] points" or "Wrong! You have lost 100 points" was presented immediately, for 2 seconds. There was then a variable delay (minimum is) before the onset of the next trial in order to establish a minimum inter-trial interval of 30 s. This feature was inserted to counteract behaviour due to delay aversion. During this delay, the current points total was presented centrally ("You have [x] points").

Reflection on the novel task was indexed by the average number of boxes opened in each condition. On each trial, it was also possible to calculate the probability of choosing correctly given the current ratio of boxes, using the formula:

Whilst this co-efficient was expected to correlate highly with the number of boxes opened, it appeared more obviously related to the levels of certainty tolerated during decision-making. The number of errors was also recorded in order to test the impact of reduced information sampling on decision-making accuracy.

Matching Familiar Figures Test (MFFT). This task was programmed in Microsoft Visual Basic and used touchscreen control. Subjects completed 2 practice trials followed by 20 trials, each with a novel template and six variants. The instructions were adapted from Sonuga-Barke et al (Sonuga-Barke et al., 1994): "In this game a picture will be shown on the screen at the same time as six similar pictures below. You have to touch one of the pictures below that is the same as the one above. Only one of the pictures is exactly the same. You will only get one go to find the right answer, and the screen will turn green if you are correct and red if you are wrong." The red or green feedback screen constituted a 1 second inter-stimulus interval before the onset of the next trial.

Statistical Analysis. Data were tested for violation of the normality assumption using the Kolmogorov-Smirnov test (all data were normally distributed). All tests employed two-tailed statistics thresholded at $p<0.05$. Internal consistency for RIT (number of boxes opened) was assessed by the correlation between odd and even numbered items, and Cronbach's alpha. Pearson's correlation coefficients were calculated for the association between the number of boxes opened and errors on RIT in the Fixed Reward and Reward Conflict conditions. Performance in the two conditions was compared directly using paired t tests. The number of boxes opened was correlated with MFFT performance (mean accuracy and latency) and BIS ratings (total, motor, attentional, non-planning). In addition, subjects were categorised as low, intermediate or high impulsivity on the MFFT, using a median split approach (Kagan, 1966). This subgrouping formed the basis for a mixed model ANOVA of RIT performance (boxes opened) with condition (Fixed Reward, Reward Conflict) as a within-subjects factor and subgroup as a between-subjects factor (3 level). A priori simple contrasts were used to compare High and Low Impulsives. One-way ANOVA was also used to explore the effect of MFFT subgrouping on BIS ratings.

Results

Figure 2:
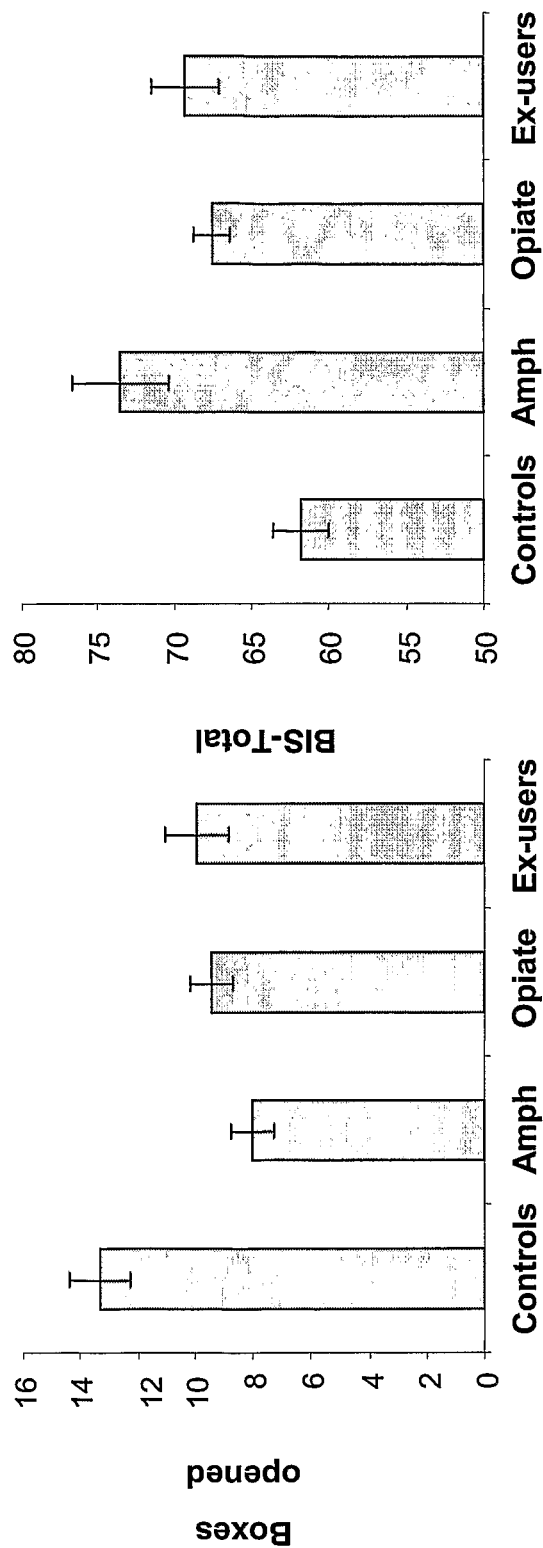
FIG. 2 shows the mean performance of the amphetamine-dependent (Amph), opiate-dependent, ex-users, and non-drug using controls on the novel reflection-impulsivity task (average number of boxes opened) and Barratt Impulsivity Scale (BIS-11). Errors bar represent SEM.

The internal reliability of the RIT was high. The correlational co-efficient of the number of boxes opened on odd versus even trials in the Fixed Reward condition was 0.95 (Cronbach's alpha=0.97) and in the Reward Conflict condition was 0.91 (Cronbach's alpha=0.95). The number of boxes opened on RIT was inversely correlated with the number of errors made in the Fixed Reward condition ($r_{40}=-0.805$, p<0.0001) and in the Reward Conflict condition ($r_{40}=-0.777$, p<0.0001), confirming the face validity of the task. Subjects opened significantly fewer boxes in the Reward Conflict condition than in the Fixed Reward condition ($t_{39}=8.35$, p<0.0001), and made significantly more errors ($t_{39}=-4.73$, p<0.0001). On the MFFT, accuracy and latency were significantly correlated ($r_{40}=0.689$, p<0.0001), but neither variable was associated with the number of boxes opened on the RIT, in either the Fixed Reward (accuracy $r_{40}=0.217$, p=0.179; latency $r_{40}=0.231$, p=0.151) or Reward Conflict (accuracy $r_{40}=0.080$, p=0.625; latency $r_{40}=0.127$, p=0.436) conditions. However, when subjects were classified on the MFFT according to a composite of accuracy and latency, this classification was significantly associated with RIT performance. Median splits on MFFT accuracy (85%) and latency (correct responses only 9556 ms) classified 12 subjects as high impulsive (fast, inaccurate), 14 subjects as low impulsive (slow, accurate) and 14 subjects as intermediate (either slow, inaccurate or fast, accurate) (see table 1 and FIG. 2). A mixed model ANOVA (condition (2 level)×MFFT subgroup (3 level)) of RIT (boxes opened) showed that subjects opened significantly fewer boxes in the Reward Conflict condition than the Fixed Reward condition (main effect of condition $F_{1,37}=68.0$, p<0.0001). There was a trend effect of MFFT subgroup ($F_{2,37}=2.84$, p=0.071), and in a planned contrast, the High Impulsive subgroup opened significantly fewer boxes than the Low Impulsive subgroup (p=0.035). The condition x group interaction was non-significant ($F_{2,37}=1.07$, p=0.353). Examining each condition separately, the effect of subgroup approached significance in the Fixed Reward condition ($F_{2,37}=3.10$, p=0.057), and the planned contrast of High vs Low Impulsives was again significant (boxes opened, $t_{37}=2.36$, p=0.024). There were no differences between MFFT subgroups in the Reward Conflict condition ($F_{2,37}=1.26$, p=0.295; planned contrast $t_{37}=1.34$, p=0.190). RIT boxes opened was closely correlated with the calculated probability of a correct decision (Fixed Reward $r_{40}=0.966$, p<0.0001; Reward Conflict, $r_{40}=0.955$, p<0.0001), and the ANOVA analysis of P(correct) by MFFT subgrouping yielded qualitatively identical results.

Scores on the BIS were not significantly correlated with the number of boxes opened on RIT in the fixed reward condition (BIS total; $r_{40}=-0.028$, p=0.864) or reward conflict condition (BIS total, $r_{40}=-0.058$, p=0.723), and were not significantly associated with MFFT subgrouping ($F_{2,37}=0.378$, p=0.688; planned contrast $t_{37}=0.693$, p=0.493) (see table 1).

The findings of experiment 1 demonstrate the reliability and validity of the novel measure. The new RIT has high internal consistency, as shown by Cronbach's alpha circa 0.95 in both task conditions. The task fulfils a core criterion for a reflection task, that the extent of information sampling is positively related to the accuracy of decision-making, as indicated by a significant negative correlation between the number of boxes opened and the number of errors, in both conditions. Healthy undergraduates showed significantly reduced information sampling in the Reward Conflict condition relative to the Fixed Reward condition. This provides indication that the certainty threshold for these decisions is flexible and sensitive to the reward contingencies of the decision. In the Fixed Reward condition, a strategy of opening boxes until 13 of one colour are revealed, ensures 100% certainty. However, these young, well-educated subjects responded at 86% certainty on average in the Fixed Reward condition. This threshold of certainty was further reduced to 74% when the reward available decreased with each box opened. The difference between the two conditions is an index of reward sensitivity in the context of information sampling.

Nevertheless, using the parameters employed in the present task, a relatively homogenous group of healthy subjects showed individual differences in the degree of information sampling, and this variability was significantly associated with a second, established measure of reflection impulsivity, the MFFT. Subjects classified as High Impulsive on the MFFT according to their speed-accuracy tradeoff (fast, inaccurate responders) showed reduced information sampling on the RIT relative to Low Impulsive subjects. These groups tolerated, on average, 80% certainty versus 90% certainty, respectively, in the Fixed Reward condition. This difference between the MFFT subgroups did not carry over to the Reward Conflict condition. This indicates that individual differences are more pronounced in the simple Fixed Reward without the added factor of reward processing. Although the MFFT and RIT aim to measure the same cognitive construct, they are aesthetically very different and the analysis variables are unrelated (errors and latency in the MFFT versus a probability in the RIT). We did not extract latency information from RIT, and accuracy information (errors) was extracted only to confirm face validity. As such, the association between the MFFT and RIT demonstrates concurrent validity for the new task, and for the construct of reflection impulsivity. It is noteworthy that neither MFFT accuracy or latency alone was significantly associated with the RIT, but the composite of accuracy and latency did reveal a significant association with RIT. This supports Kagan's original notion that MFFT accuracy and latency are both important in the determination of reflection impulsivity.

Experiment 2

Methods

A total of 105 volunteers were recruited via advertisement and word of mouth. Subjects completed written informed consent prior to testing, which was approved by the Local Research Ethics Committee. Subjects were grouped as follows: i) 22 individuals with a DSM-IV diagnosis of (current) substance dependence to amphetamine (amph), ii) 36 individuals with a DSM-IV diagnosis of (current) substance dependence to opiates, iii) 23 individuals with a DSM-IV diagnosis of (previous) substance dependence to either amphetamines or opiates ("Ex-users"), who had been abstinent for at least one year, and iv) 24 non-drug using control subjects. Group characteristics are displayed in table 2. No subjects were receiving current psychiatric treatment, and no subjects had suffered overdose requiring overnight hospital admission. Amph and opiate users did not meet criteria for substance dependence to any substance besides amphetamines and opiates, respectively, but many subjects reported current or past abuse of other substances, detailed in table 3. Urine analysis was performed on the day of participation with the SureStep Drug Screen Test (Euromed Limited, London U.K.) to test for amphetamine, cocaine, benzodiazepines, methadone and morphine use. In the amph group, 21/22 tested positive for amphetamine, but only 13 subjects tested positive for amphetamine alone (additional substances: 6 morphine, 2 benzodiazepines, 2 cocaine). The window of detection for amphetamine in urine was only 1-2 days, and therefore the single subject who tested negative for amphetamine was nonetheless included in the group. In the opiate group, 36/36 subjects tested positive for morphine or methadone (7 methadone only, 2 morphine only, 3 methadone and morphine), with an additional 15 subjects positive for cocaine, 12 subjects positive for benzodiazepines and 1 subject positive for amphetamine. Urine analysis of the ex-users and non-drug using controls were negative for all substances. Ex-users reported abstinence for a mean of 8.4 years, continuously (sd 6.1, range 1-18) and were members of narcotics anonymous. In the non-drug using controls, 4 subjects reported previous social experiences of cannabis, 4 were current cigarette smokers, and 9 had quit smoking cigarettes.

Subjects were administered the RIT and BIS-11 (see Experiment 1) as part of a larger neuropsychological test battery reported elsewhere. There was missing BIS-11 data on 4 amph subjects, 1 opiate subject and 1 ex-user.

Statistical Analysis

Data were tested for violation of the normality assumption using the Kolmogorov-Smirnov test (all variables were normally distributed). All tests employed two-tailed statistics thresholded at $p<0.05$. A repeated-measures ANOVA was used to test group differences on the RIT with a within-subjects factor of task condition (Fixed Reward, Reward Conflict) and a between-subjects factor of group (4 level). One-way ANOVAs (4 level) were used to explore group differences on the BIS-11. Pearson's correlations were calculated for each group separately, to assess the relationships between RIT performance, BIS ratings, and the duration (in years) and age of onset of drug abuse.

Results

Figure 3:
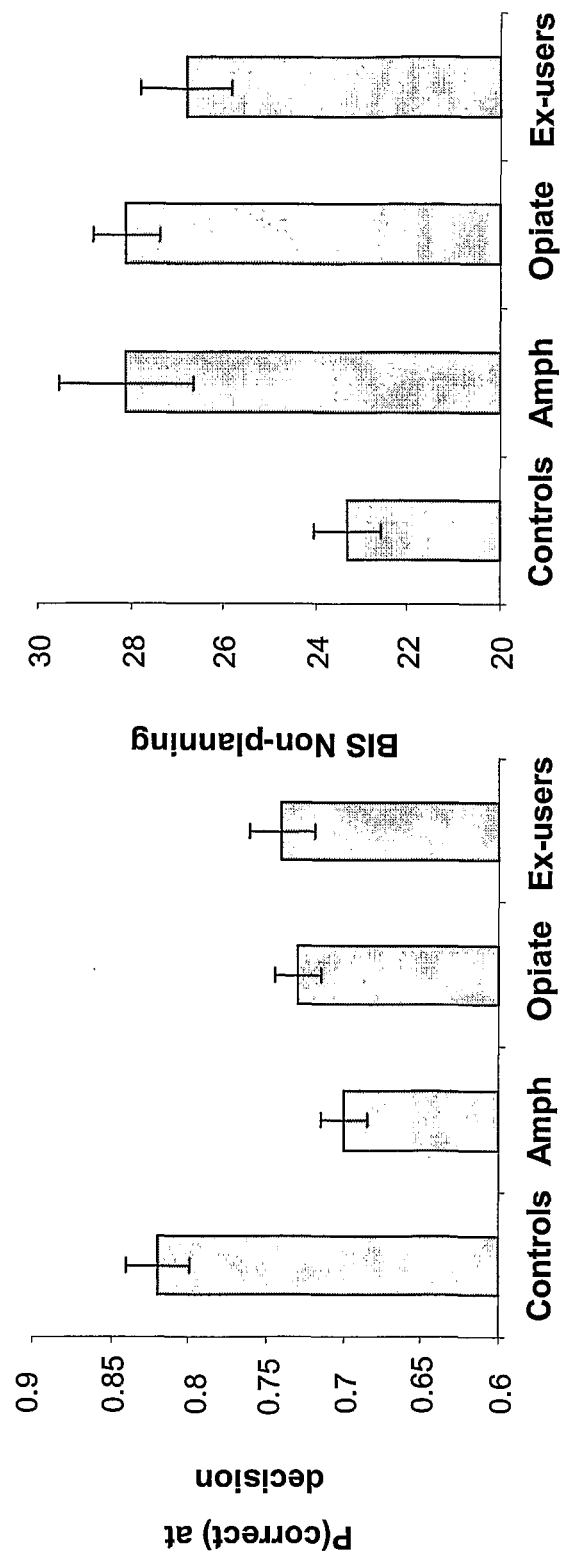
FIG. 3 shows the mean performance of the amphetamine-dependent (Amph), opiate-dependent, ex-users, and non-drug using controls on the novel reflection-impulsivity task (probh of correct decision) and Barratt Impulsivity Scale (BIS-11). Errors bar represent SEM.

One-way ANOVA of age, verbal IQ and BDI-II depression ratings revealed a significant group effect on BDI ratings ($F_{3,101}=10.5$, $p<0.0001$) due to increased levels of depression in the amph and opiate groups relative to controls (Tukey's $p<0.004$ and $p<0.0001$ respectively), and a trend effect on age ($F_{3,101}=2.70$, $p=0.050$) due to a significant difference between the opiate and ex-user groups ($p=0.049$) (see table 2). Age and BDI ratings were entered as covariates in the mixed model ANOVA of RIT performance (boxes opened) which revealed a significant main effect of RIT condition ($F_{1,99}=9.90$, $p=0.002$), such that subjects opened fewer boxes in the Reward Conflict condition than the Fixed Reward condition. There was also a significant main effect of group ($F_{3,99}=4.13$, $p=0.008$) and a significant group x condition interaction ($F_{3,99}=3.14$, $p=0.029$). The effects of age ($F_{1,99}=2.61$, $p=0.110$) and BDI rating ($F_{1,99}=0.028$, $p=0.867$) were not significant. To further elucidate the nature of the group effects, the two conditions were analysed separately (see table 4). In the Fixed Reward condition (see FIG. 3), there was a significant effect of group ($F_{3,101}=5.45$, $p=0.002$) due to reduced reflection in the amph (Tukeys $p=0.001$), opiate (Tukeys $p=0.011$) and, at trend, in the ex-users (Tukeys $p=0.073$) relative to the non-drug using controls. The ex-user group did not differ from the amph ($p=0.517$) or opiate ($p=0.975$) groups. There was no significant group effect in the Reward Conflict condition ($F_{3,101}=1.19$, $p=0.317$). From table 4, it is clear that the significant group x condition interaction term in the mixed model ANOVA reflects a 'floor effect', whereby the discrepancy between the Fixed Reward and Reward Conflict conditions in the controls must be of reduced magnitude in the three drug use groups because of reduced reflection in the Fixed Reward condition. Paired t tests revealed a significant difference between Fixed Reward and Reward Conflict conditions in all four groups of subjects (all $p<0.05$), indicating that all four groups are broadly sensitive to the reward contingencies of the two conditions and are motivated to win points on the task.

One-way ANOVAs of BIS-11 ratings revealed significant group effects on the total score ($F_{3,95}=5.46$, $p=0.002$), and on the attentional ($F_{3,95}=8.10$, $p<0.0001$) and non-planning ($F_{3,95}=6.07$, $p=0.001$) subscales, but not on the motor subscale ($F_{3,95}=1.98$, $p=0.122$). Post-hoc tests (Tukeys) showed significantly inflated scores (relative to controls) in the amph group on the BIS total ($p=0.001$), attentional ($p=0.001$) and non-planning ($p=0.006$) scales, in the opiate group on the BIS non-planning subscale ($p=0.001$) only, and in the ex-users on the BIS total ($p=0.046$) and attentional ($p=0.015$) subscale. The only significant post-hoc comparison between drug groups was on the attentional subscale, where both amph and ex-users scored significantly higher than the opiate group ($p=0.001$ and $p=0.021$ respectively).

There was no significant negative association between RIT performance and BIS ratings (total or any BIS subscale) in either the separate groups (all $r>-0.21$) or across all groups (e.g. BIS total $r_{99}=-0.046$, $p=0.652$). RIT performance was unrelated to the duration of drug abuse (amph $r_{22}=-0.121$, $p=0.592$; opiate $r_{36}=-0.107$, $p=0.534$; ex-user $r_{2.3=0.188}$, $p=0.389$) and the age of onset of drug taking (amph $r_{22}=0.081$, $p=0.720$; opiate $r_{36}=-0.179$, $p=0.326$; ex-user $r_{23}=0.339$, $p=0.144$).

The RIT was highly sensitive to substance dependence in two groups with amphetamine dependence and opiate dependence, in comparison to non-drug using control subjects. The amphetamine- and opiate-dependent subjects sampled less information (in terms of boxes opened) and tolerated a lower probability of making a correct response in the Fixed Reward condition of the novel task. In this condition, subjects are free to sample information up to a point of 100% response certainty with no associated costs. Very few controls or drug users consistently implemented this strategy, but controls make their decision at an average probability of 0.80, whereas the amphetamine- and opiate-dependent groups made their decisions at an average probability of 0.70 and 0.73 respectively. The effect size (d) for the amphetamine-control comparison was 1.38 and for the opiate-control comparison was 0.96, which both represent large effect sizes (Cohen, 1988). A third group of subjects with a prior history of either amphetamine or opiate dependence, who had abstained from drug administration for at least one year, also showed reduced reflection on the task. Whilst the post-hoc comparison between ex-users and controls reached only marginal significance ($p=0.07$), the effect size for this difference was 0.80 (a large effect) and average scores were close to the amphetamine and opiate dependent groups. These ex-users had abstained from drugs for an average of 8 years, indicating that prolonged abstinence provides minimal recovery in this cognitive domain.

These two experiments demonstrate the validity and sensitivity of a novel computerised measure of reflection-impulsivity designed for use in adult neuropsychological and psychiatric research. The RIT has strong internal consistency and is associated with an established test of reflection, the MFFT, in undergraduate students. Significant reductions in reflection were shown in two groups of subjects with chronic substance dependence to amphetamines and opiates. These subjects also showed inflated self-report ratings of impulsivity on the BIS, and yet in both experiments 1 and 2, there was no relationship between laboratory measurement of reflection with the RIT and BIS ratings.

TABLE 1

|  | | MFFT Impulsivity subgrouping | | |
|---|---|---|---|---|
|  | Overall | Low | Intermediate | High |
| N | 40 | 14 | 14 | 12 |
| MFFT-accuracy | 85.0 (10.8) | 94.6 (4.58) | 86.8 (5.41) | 71.7 (6.15) |
| MFFT-latency | 9.98 (3.93) | 13.6 (2.89) | 9.62 (2.86) | 6.09 (1.05) |
| BIS-Total | 69.3 (10.3) | 69.9 (8.9) | 70.4 (12.9) | 67.1 (8.8) |
| BIS-Attentional | 19.5 (4.9) | 20.1 (4.3) | 20.9 (6.3) | 17.3 (2.9) |
| BIS-Motor | 24.1 (3.7) | 23.8 (3.1) | 24.5 (4.3) | 23.8 (3.7) |

TABLE 1-continued

| | | MFFT Impulsivity subgrouping | | |
|---|---|---|---|---|
| | Overall | Low | Intermediate | High |
| BIS-Nonplanning | 25.6 (4.6) | 26.0 (5.4) | 24.8 (4.6) | 26.1 (3.7) |
| RIT-Fixed Reward | | | | |
| Boxes | 15.7 (5.8) | 17.5 (6.0)† | 16.6 (4.9) | 12.4 (5.5) |
| $P_{correct}$ | .86 (.11) | .90 (.11)† | .87 (.10) | .80 (.12) |
| Errors | 1.23 (1.2) | .86 (.86) | 1.14 (1.03) | 1.75 (1.48) |
| RIT-Reward Conflict | | | | |
| Boxes | 9.1 (4.3) | 9.7 (4.5) | 9.9 (4.9) | 7.5 (3.2) |
| $P_{correct}$ | .74 (.08) | .76 (.09) | .74 (.09) | .71 (.07) |
| Errors | 2.4 (1.8) | 1.9 (1.8) | 2.36 (1.8) | 3.1 (1.6) |

†planned contrast of High versus Low Impulsives $p < .05$

TABLE 2

| | Controls | Amphetamine | Opiate | Ex-users |
|---|---|---|---|---|
| N | 24 | 22 | 36 | 23 |
| Age | 36.0 (9.0) | 37.8 (7.9) | 33.6 (7.5) | 39.0 (5.9) |
| Gender M:F | 12:12 | 12:10 | 29:7 | 13:10 |
| Verbal IQ | 114.4 (6.8) | 110.9 (5.3) | 112.5 (6.1) | 114.1 (7.4) |
| BDI-II | 3.96 (3.0) | 12.4 (8.1) | 15.4 (10.2) | 8.0 (8.2) |
| Years abuse | — | 17.2 (9.4) | 11.6 (8.8) | 10.7 (5.3) |
| Age of onset amphetamines | — | 18.9 (5.3) | 18.1 (4.4) $^{n=30}$ | 17.1 (2.9) $^{n=20}$ |
| Age of onset opiates | — | 26.5 (8.3) $^{n=13}$ | 21.3 (3.6) | 20.0 (4.2) $^{n=19}$ |

TABLE 3

| | | Controls | Amphetamine | Opiate | Ex-users |
|---|---|---|---|---|---|
| Amphetamine | Current | 0.0 | 100.0 | 0.0 | 0.0 |
| | Past | 0.0 | 100.0 | 83.3 | 87.0 |
| Opiates | Current | 0.0 | 9.1 | 100.0 | 0.0 |
| | Past | 0.0 | 59.1 | 100.0 | 82.6 |
| Ecstasy (MDMA) | Current | 0.0 | 13.6 | 2.8 | 0.0 |
| | Past | 0.0 | 63.6 | 69.4 | 52.2 |
| Cocaine | Current | 0.0 | 45.5 | 58.3 | 0.0 |
| | Past | 0.0 | 90.1 | 100 | 95.6 |
| Benzodiazepines | Current | 0.0 | 9.1 | 8.3 | 0.0 |
| | Past | 0.0 | 50.0 | 83.3 | 69.6 |
| Hallucinogens | Current | 0.0 | 9.1 | 0.0 | 0.0 |
| | Past | 0.0 | 77.3 | 83.3 | 78.2 |
| Cannabis | Current | 0.0 | 63.6 | 50.0 | 0.0 |
| | Past | 0.0 | 81.8 | 97.2 | 87.0 |
| Alcohol | Current | 0.0 | 9.1 | 11.1 | 0.0 |
| | Past | 0.0 | 31.8 | 61.1 | 87.0 |
| Nicotine | Current | 16.7 | 95.4 | 94.4 | 47.8 |
| | Past | 54.2 | 100 | 100 | 91.3 |

TABLE 4

| | Controls | Amphetamine | Opiate | Ex-users |
|---|---|---|---|---|
| Fixed Reward | | | | |
| Boxes | 13.3 (5.2) | 8.0 (3.6) | 9.4 (4.4) | 9.9 (5.2) |
| Prob (correct) | .82 (.10) | .70 (.07) | .73 (.09) | .74 (.10) |
| Errors | 1.5 (1.3) | 2.8 (1.1) | 2.3 (1.0) | 2.3 (1.8) |

TABLE 4-continued

| | Controls | Amphetamine | Opiate | Ex-users |
|---|---|---|---|---|
| Reward Conflict | | | | |
| Boxes | 7.4 (2.9) | 5.8 (3.2) | 6.7 (2.5) | 6.4 (3.4) |
| Prob (correct) | .69 (.06) | .66 (.06) | .68 (.06) | .68 (.06) |
| Errors | 2.9 (1.5) | 3.6 (1.5) | 3.1 (1.5) | 3.4 (1.5) |
| BIS-Total | 61.8 (8.8) | 73.5 (13.5) | 67.5 (6.9) | 69.3 (10.2) |
| BIS-Attentional | 14.5 (3.2) | 18.6 (3.8) | 14.9 (3.0) | 17.6 (3.6) |
| BIS-Motor | 23.9 (3.8) | 26.8 (5.5) | 24.6 (3.0) | 24.9 (3.7) |
| BIS-Nonplanning | 23.3 (3.5) | 28.1 (6.2) | 28.1 (4.1) | 26.8 (4.6) |

REFERENCES

Allen T J et al Drug Alcohol Depend 1998; 50: 137-45.
Aron A R, et al. Trends Cogn Sci 2004; 8: 170-177.
Ault R L, et al Child Dev. 1976; 47: 227-231.
Barratt E S. Psychological Reports 1965; 16: 547-554.
Bentler P M, McClain J. Child Dev. 1976; 47: 218-226.
Bickel W K, Marsch L A. Addiction 2001; 96: 73-86.
Block J, et al Dev. Psychol. 1974; 10: 611-632.
Brown R T et al. Pediatrics 1979; 64: 408-11.
Carrillo-de-la-Pena M T, et al Perc. Mot. Skills 1993; 77: 567-575.
Cohen J. Power analysis for the behavioural sciences; 1988.
Cowan R L et al. Drug Alcohol Depend 2003; 72: 225-35.
Daruna J H, Barnes P A. A neurodevelopmental view of impulsivity. In: Schur M B, editor. The impulsive client: theory, research and treatment. Washington, D.C.: American Psychological Association; 1993.
Dawes M A, et al. Drug Alcohol Depend 1997; 45: 165-76.
Di Chiara G et al Proc Natl Acad Sci USA 1988; 85: 5274-8.
Dickman S J. J Pers Soc Psychol 1990; 58: 95-102.
Eisen S V et al J. Adolesc. Res. 1992; 7: 250-265.
Evenden J L. Psychopharmacology 1999; 146: 348-61.
Fillmore M T, Rush C R. Drug Alcohol Depend 2002; 66: 265-73.
Fox H C, et al Psychopharmacology (Berl) 2002; 162: 203-14.
Jentsch J D, et al Neuropsychopharmacology 2002; 26: 183-90.
Kagan J. J Abnorm Psychol 1966; 71: 17-24.
Koob G F et al Science 1988; 242: 715-23
Liu X et al. Neuropsychopharmacology 1998; 18: 243-52.
Logan G et al. In: Dagenbach D & Carr T, Inhibitory processes in attention, memory and language. Cambridge Mass., MIT Press, 2000.
Matochik J A et al. Neuroimage 2003; 19: 1095-102.
Mazur J. An adjusting procedure for studying delayed reinforcement. In: ML Commons M J, Nevin J A, Rachlin H, editor. Quantitative analysis of behavior. Vol 5: the effect of delay and of intervening events on reinforcement value. Hillsdale, N.J.: Erlbaum; 1987.
Messer S B. Psychol. Bull. 1976; 83: 1026-1052
Moeller F G, et al. Am J Psychiatry 2001; 158: 1783-93.
Moeller F G et al Drug Alcohol Depend 2002; 68: 105-11.
Morgan M J. Neuropsychopharmacology 1998; 19: 252-64.
Morgan M J et al Psychopharmacology (Berl) 2002; 159: 294-303.
Ornstein T J et al. Neuropsychopharmacology 2000; 23: 113-26.
Patton J H, et al J Clin Psychol 1995; 51: 768-74.

Paulus M P, et al. Biol Psychiatry 2003; 53: 65-74.
Potenza M N. Semin Clin Neuropsychiatry 2001; 6: 217-26.
Rapeli P et al. Memory 1997; 5: 741-62.
Roberts A C, et al. Cereb Cortex 2000; 10: 252-62.
Rogers R D, et al Neuropsychopharmacology 1999; 20: 322-29.
Salo R, et al Psychiatry Res 2002; 111: 65-74.
Sandoval J. Rev. Educ. Res. 1977; 47: 293-318.
Sekine Y, et al Am J Psychiatry 2003; 160: 1699-701.
Sonuga-Barke E J et al J Child Psychol Psychiatry 1994; 35: 1247-53.
Swann A C et al. Biol Psychiatry 2002; 51: 988-94.
Tarter R E et al Drug Alcohol Depend 2004; 73: 121-32.
Volkow N D et al Am J Psychiatry 2001; 158: 2015-21.
Wang G J et al Neuropsychopharmacology 1997; 16: 174-82.
Wang G J et al Lancet 2001; 357: 354-7.
Whiteside S P et al. Pers. Ind. Diff. 2001; 30: 669-689.
Wilson J M et al Nat Med 1996; 2: 699-703.

The invention claimed is:

1. A method of assessing an individual using a computer, comprising;
   displaying on a display unit of the computer a population of elements to the individual,
   allowing the individual to select an element from the population using an input unit of the computer,
   revealing to the individual on the display unit a characteristic of the element selected,
   the characteristic being one of a set of possible characteristics for elements in the population,
   allowing the individual to select using the input unit at least one additional element from the population;
   revealing to the individual a characteristic of the additional element selected;
   allowing the individual to decide which of the characteristics from the set is possessed by a majority of the elements in the population and to select the decided characteristic using the input unit of the computer; and
   correlating the number of elements selected by the individual before selecting the characteristic decided to be possessed by the majority, with a probability that the individual has an impulsivity associated cognitive dysfunction.

2. A method according to claim 1, wherein the set of possible characteristics consists of two characteristics.

3. A method according to claim 1, wherein each characteristic in the set of possible characteristics is a color.

4. A method according to claim 1, wherein the population comprises 25 elements.

5. A method according to claim 4, wherein the population is arranged in a 5×5 matrix.

6. A method according to claim 1, wherein each element in the population is a square.

7. A method according to claim 1, wherein the population is displayed on an image display.

8. A method according to claim 1, further comprising recording the characteristic which the individual decides is possessed by the majority of the elements in the population.

9. A method according to claim 8, wherein the complete set of characteristics are displayed and the characteristic is recorded by choosing the characteristic from the displayed set of characteristics.

10. A method according to claim 9, wherein the characteristic is chosen via a graphic interface.

11. A method according to claim 10, wherein the graphic interface comprises a touch sensitive screen.

12. A method according to claim 1, further comprising determining the numbers of elements possessing each characteristic which were selected by the individual.

13. A method according to claim 12, comprising calculating a probability of a correct response from said numbers of elements.

14. A method according to claim 1, wherein the individual is awarded points for choosing the correct characteristic.

15. A method according to claim 14, wherein the individual loses points for choosing an incorrect characteristic.

16. A method according to claim 14 wherein the individual loses points for each additional element selected from the population.

17. A method according to claim 14, wherein the number of points accrued by the individual is displayed.

18. A method for assessing an individual using a computer, comprising:
   performing a test a predetermined number of times to determine if an individual has an impulsivity associated cognitive dysfunction, the test comprising:
      notifying the individual that each element of the population has one characteristic from a set of characteristics and that the individual should try to determine which one of these characteristics is the characteristic possessed by a majority of the elements in the population,
      allowing the individual to select an element from the population using an input unit of the computer,
      revealing to the individual on the display unit a characteristic of the element selected,
      allowing the individual to select using the input unit at least one additional element from the population,
      revealing to the individual a characteristic of the additional element selected;
      allowing the individual to select a characteristic decided to be possessed by a majority of the elements in the population using the input unit of the computer, and
   correlating the number of elements selected by the individual in a test with a probability that the individual has an impulsivity associated cognitive dysfunction.

19. A method according to claim 18, wherein the test is performed 10 times.

20. A method according to claim 18 wherein a total number of incorrect decisions made by the individual is determined and an error rate determined.

21. A method according to claim 18, wherein an average number of elements selected by the individual before making a decision is determined.

22. A method according to claim 18, further comprising determining an average probability of a correct response when the individual chooses a characteristic.

23. A method according to claim 22, wherein a reduced average probability relative to a healthy control is indicative of impulsivity associated cognitive dysfunction.

24. A method according to claim 22, wherein an average probability of less than 0.77 is indicative of an impulsivity associated cognitive dysfunction.

25. A method according to claim 1, wherein the impulsivity associated cognitive dysfunction is selected from the group consisting of substance abuse and attention deficit hyperactive disorder.

26. A method of identifying and/or obtaining a compound useful in the treatment of impulsivity associated cognitive dysfunction using a computer, the method comprising;
   administering a test compound to an individual,
   displaying on a display unit of the computer a population of elements to the individual, allowing the individual to select an element from the population using an input unit of the computer, revealing to the individual on the display unit a characteristic of the element selected, the characteristic being one of a set of possible characteristics for elements in the population, allowing the individual to select using the input unit at least one additional element from the population;

revealing to the individual a characteristic of the additional element selected, wherein the selection and revealing process is repeated until the individual decides which of the characteristics from the set is possessed by a majority of the elements in the population, correlating the number of elements selected by the individual with a probability that the individual has an impulsivity associated cognitive dysfunction, and determining based on the correlation an impulsivity of the individual.

27. A method according to claim 26, wherein the test compound is administered to a population of individuals.

28. A method of assessing a treatment for impulsivity associated cognitive dysfunction using a computer, the method comprising;

displaying on a display unit of the computer a population of elements to the individual, allowing the individual to select an element from the population using an input unit of the computer, revealing to the individual on the display unit a characteristic of the element selected, the characteristic being one of a set of possible characteristics for elements in the population, allowing the individual to select using the input unit at least one additional element from the population;

revealing to the individual a characteristic of the additional element selected;

allowing the individual to decide which of the characteristics from the set is possessed by a majority of the elements in the population and to select the decided characteristic using the input unit of the computer, correlating the number of elements selected by the individual with a probability that the individual has an impulsivity associated cognitive dysfunction, determining based on the correlation an impulsivity of an individual being treated for impulsivity associated cognitive dysfunction at a first time point and at a second time point, and determining changes in the impulsivity at the first time point and at the second time point.

29. A computer system for assessing a treatment for impulsivity associated cognitive dysfunction, the computer system comprising a display unit and a processor to perform:

displaying on the display unit a population of elements to the individual, allowing the individual to select an element from the population using an input unit of the computer system, revealing to the individual on the display unit a characteristic of the element selected, the characteristic being one of a set of possible characteristics for elements in the population, allowing the individual to select using the input unit at least one additional element from the population;

revealing to the individual a characteristic of the additional element selected;

allowing the individual to decide which of the characteristics from the set is possessed by a majority of the elements in the population and to select the decided characteristic using the input unit of the computer, and correlating the number of elements selected by the individual before selecting the characteristic decided to be possessed by the majority in the population, with a probability that the individual has an impulsivity associated cognitive dysfunction.

30. A computer system according to claim 29, comprising a graphic interface to allow a selection of elements in the population and a registration of the characteristic which the individual decides is possessed by the majority of the elements in the population.

31. A computer system according to claim 30, wherein the graphic interface comprises a touch sensitive monitor.

32. A non-transitory computer readable medium comprising a computer executable code to execute:

displaying on the display unit a population of elements to the individual, allowing the individual to select an element from the population using an input unit of the computer system, revealing to the individual on the display unit a characteristic of the element selected, the characteristic being one of a set of possible characteristics of elements in the population, allowing the individual to select using the input unit at least one additional element from the population;

revealing to the individual a characteristic of the additional element selected;

allowing the individual to decide which of the characteristics from the set is possessed by a majority of the elements in the population and to select the decided characteristic using the input unit of the computer, and correlating the number of elements selected by the individual with a probability that the individual has an impulsivity associated cognitive dysfunction.

33. A computer system configured to perform:

displaying on the display unit a population of elements to the individual, allowing the individual to select an element from the population using an input unit of the computer system, revealing to the individual on the display unit a characteristic of the element selected, the characteristic being one of a set of possible characteristics for elements in the population, allowing the individual to select using the input unit at least one additional element from the population;

revealing to the individual a characteristic of the additional element selected, wherein the selection and revealing process is repeated until the individual decides which of the characteristics from the set is possessed by a majority of the elements in the population, and correlating the number of elements selected by the individual with a probability that the individual has an impulsivity associated cognitive dysfunction.

34. A test device for assessing an individual for an impulsivity associated cognitive disorder, comprising:

a display, a graphic interface, and a processor configured to perform:

displaying on the display unit a population of elements to the individual, allowing the individual to select an element from the population using an input unit of the computer system, revealing to the individual on the display unit a characteristic of the element selected, the characteristic being one of a set of possible characteristics for elements in the population, allowing the individual to select using the input unit at least one additional element from the population;

revealing to the individual a characteristic of the additional element selected;

allowing the individual to decide which of the characteristics from the set is possessed by a majority of the elements in the population and to select the decided characteristic using the input unit of the computer, and correlating the number of elements selected by the individual with a probability that the individual has an impulsivity associated cognitive dysfunction.

\* \* \* \* \*